United States Patent
Doerr et al.

(10) Patent No.: US 8,521,254 B2
(45) Date of Patent: Aug. 27, 2013

(54) MRT LORENTZ VIBRATOR

(75) Inventors: Thomas Doerr, Berlin (DE); Ingo Weiss, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 381 days.

(21) Appl. No.: 12/972,453

(22) Filed: Dec. 18, 2010

(65) Prior Publication Data

US 2011/0152733 A1  Jun. 23, 2011

Related U.S. Application Data

(60) Provisional application No. 61/288,860, filed on Dec. 22, 2009.

(51) Int. Cl.
  *A61B 5/05*  (2006.01)
(52) U.S. Cl.
  USPC ........... 600/407; 600/410; 600/411; 600/425; 600/427
(58) Field of Classification Search
  USPC .......................... 600/407, 410, 411, 425, 427
  See application file for complete search history.

(56) References Cited

U.S. PATENT DOCUMENTS

| | | | | |
|---|---|---|---|---|
| 4,120,307 A | * | 10/1978 | Jirak et al. | ........................ 607/29 |
| 5,309,096 A | * | 5/1994 | Hoegnelid | .................... 324/256 |
| 5,751,904 A | | 5/1998 | Inazumi | |
| 6,125,290 A | * | 9/2000 | Miesel | ........................... 600/325 |
| 6,477,398 B1 | * | 11/2002 | Mills | .............................. 600/409 |
| 2002/0133086 A1 | * | 9/2002 | Connelly et al. | .............. 600/509 |
| 2003/0083570 A1 | * | 5/2003 | Cho et al. | ....................... 600/410 |
| 2006/0265139 A1 | | 11/2006 | van der Weide et al. | |
| 2007/0176596 A1 | | 8/2007 | Garcia et al. | |
| 2008/0154342 A1 | | 6/2008 | Digby et al. | |

FOREIGN PATENT DOCUMENTS

| | | |
|---|---|---|
| EP | 0702981 A1 | 3/1996 |
| WO | WO 9412238 A1 | 6/1994 |
| WO | WO 03037429 A1 | 5/2003 |
| WO | WO 2006121546 A1 | 11/2006 |

OTHER PUBLICATIONS

European Search Report dated Apr. 26, 2011 (9 pages).

* cited by examiner

*Primary Examiner* — Peter Luong
(74) *Attorney, Agent, or Firm* — Arc IP Law, PC; Joseph J. Mayo

(57) ABSTRACT

A device and a method for recognizing electromagnetic fields, specifically those fields that occur in image-guided nuclear spin tomography examinations (hereinafter MRT or MRI). In particular, it relates to an implantable medical device (IMD) containing a unit for detecting MRT activity, whereby the unit for the detection of MRT activity consists of at least one vibration transducer that transforms vibrations and/or oscillations caused by an MRT device into an electrical or optical signal and the unit for detecting MRT activity recognizes an MRT activity because of this signal.

15 Claims, 4 Drawing Sheets

MRT LORENTZ VIBRATOR

This application claims the benefit of U.S. Provisional Patent Application 61/288,860, filed on Dec. 22, 2009, which is hereby incorporated by reference in its entirety.

BACKGROUND OF THE INVENTION

1. Field of the Invention

Embodiments of the invention relate to a device and a method for recognizing electromagnetic fields, specifically those fields that occur in image-guided nuclear spin tomography or magnetic resonance tomography devices. ("MRT" or "MRI" stand for magnetic resonance tomography and magnetic resonance imaging respectively, wherein these two acronyms are used interchangeably herein).

2. Description of the Related Art

Although MRI examinations are becoming increasingly important in diagnostic medicine, some patients are contraindicated for MRI examinations. Such a contraindication can be the result of an at least partially implanted medical device (hereinafter also implant or IMD).

To make MRI examinations possible in spite of that, various methods are known that relate either to the performance of the MRI examination or to the implantable medical device.

Among others, technologies for the recognition of magnetic fields are known that are based on conventional methods of magnetic field detection. Thus, US 2008/0154342, describes a method using a GMR sensor (Giant Magnetic Resistance), in order to recognize problematic magnetic fields of MRT devices. However, these technical approaches are not very specific and generate an increased energy requirement, which leads to a shorter service life at the same energy reserves.

Systems are also known in prior art that use the change of vibration parameters for the determination of changes of the strength of magnetic fields for periodically vibrating systems, as is described in US 2006/0265139. Because of the general conditions, such as, for example, the periodic vibration, such systems are not suitable for the detection of magnetic fields in the area of implants.

BRIEF SUMMARY OF THE INVENTION

It is therefore the object of embodiments of the invention to provide a device and a method for medical devices and implantable medical devices that eliminate the disadvantages of prior art and permit the reliable recognition of electromagnetic fields. The object is solved by an implantable medical device (IMD) that has the characteristics as claimed herein.

The implantable medical device (IMD) thereby contains a unit for detecting MRT activity, whereby the unit for detecting MRT activity includes at least one vibration transducer, that transforms vibrations and/or oscillations created by an MRT device into an electric and/or optical signal and the unit for detecting MRT activity recognizes MRT activity based on this signal.

In this context, MRT activity is to be understood as the electromagnetic noise fields and other mechanical effects that occur when an MRT device is used. These include, for example, but not exclusively, static electromagnetic fields, electromagnetic gradient fields and/or radio frequency fields, but also mechanical vibrations that are caused by alternating electromagnetic fields and/or mechanically moved objects, but not limited to the movable examination table.

In the context of electromagnetic fields and/or movable objects, characteristic vibrations and/or oscillations occur at the MRT device as well as in the IMD. The vibrations and/or oscillations in the IMD can thereby be transmitted by mechanical coupling to the IMD as well as be induced by electromagnetic fields or be induced by electromagnetic fields in components. These components can be conventional components of an IMD or also be configured specifically for the recognition of vibrations and/or oscillations.

It is preferred, that based on the recognition of MRT activity, an operating mode is selected for the IMD, that permits safe operation in the presence of MRT activity.

It is also preferred that the vibrations are transmitted by means of Lorentz forces by electromagnetic fields from the MRT device to the vibration transducer and/or that the vibrations as a result of Lorentz forces are transmitted by electromagnetic fields from the MRT device to the IMD and from there are transmitted to the vibration transducer and/or that the vibrations are created in the MRT device and these are mechanically transmitted to the vibration transducer, whereby the vibration transducer can be configured for various types of transmission and/or separate vibration transducers can be provided for the respectively different transmission types. Separate vibration transducers are provided with at least varying sensitivities for detecting different oscillations and/or vibrations.

It is also preferred that at least one vibration transducer is adjusted to the typical frequency spectrum for MRT noises for the MRT device.

All those noises are described as MRT noise that are typically created when the MRT device is used, such as vibrations and/or oscillations induced in the MRT device as the result of Lorentz forces, and/or vibrations and/or oscillations caused by automated, mechanical motions.

Moreover, it is preferred that at least one vibration transducer can also be used as acceleration sensor and this acceleration sensor is usable for the rate-adaptive stimulation of a cardiac pacemaker and/or defibrillator/cardioverter and/or cardiac resynchronization device.

It is also preferred that the vibration transducer is housed in a helium-tight and/or evacuated housing. The helium-tightness and the evacuation thereby prevent and/or decrease the subsequent penetration of helium into the housing and thus minimize dampening effects of the vibration transducer.

It is also preferred that at least one vibration transducer can be put into vibration according to the Lorentz force always only then, when a magnetic field with a predeterminable minimum field strength is present simultaneously and eddy currents are induced by alternating magnetic fields.

Preferred is also that at least one vibration transducer is connected mechanically with a high tension transformer.

High tension transformers can be provided in devices such as defibrillators/cardioverters.

It is also preferred that at least one vibration transducer can be connected with a programming coil of the IMD, so that the programming coil can be put into vibration as the result of MRT activity, these vibrations can be transmitted to the vibration transducer and the resonance behavior of the programming coil can be adjusted for typical MRT activities.

It is further preferred that at lest one vibration transducer consists of a piezoelectric core surrounded by a coil, whereby the coil puts the piezoelectric core into vibration as the result of Lorentz forces and thus generates a piezoelectric signal which is usable as signal for the detection of MRT.

It is also preferred that at least one vibration transducer consists of an accelerator sensor as core that is surrounded by a coil, whereby the core of the coil can be put into vibration as a result of Lorentz forces.

It is likewise preferred that at least one vibration transducer observes typical MRT noises by means of at least one microphone and/or at least one acceleration sensor, that the observed MRT noises can be filtered and subsequently associated with typical MRT noise sequences by autocorrelation in a digital signal processor (DSP).

It is also preferred that at least the signals of the vibration transducer are processed by means of a voice recognition procedure that is adapted to MRT noise recognition and/or a neural network such as "parallel comparison of structures".

It is further preferred that at least one of the following steps is a part of the safe operating condition in the presence of MRT activity, the changing into an MRI-safe condition, an extended stay in an MRI-safe or with respect to electromagnetic interference fields insensitive condition, the delivery of electromagnetic pulses for signaling that a medical device, specifically an implant is present in the electromagnetic field, specifically for signaling to an MRI device, with the possibility of transmitting, in addition to the interference, also information in this manner and to make such visible on the monitor, and the delivery of a therapy and/or detection of electrical conditions of the tissue is allowed only in timeframes in which no electromagnetic interference fields are recognized and/or that a reconstruction of measurements is performed for the sections in which the detection is not permitted because of recognized electromagnetic interference fields.

It is also preferred that the unit for detecting MRT activity comprises at least one of the following sensors or indicators: GMR sensor, MagFET sensor, Hall sensor, electro-optical transducer as indicator, the monitoring of battery voltage during capacitor loading processes as indicator, the detection of RF fields as indicator, the detection of magnetic gradient fields as indicator, and the detection of currents that are induced by electromagnetic fields as indicator.

This problem is also solved by a method for detecting MRT activity, whereby a vibration transducer transforms vibrations and/or oscillations caused by an MRT device into an electric and/or optical signal and a unit for detecting MRT activity recognizes MRT activity because of this signal. A combination of this method with other examples of embodiments is possible explicitly.

BRIEF DESCRIPTION OF THE DRAWINGS

Several aspects of the invention are illustrated in FIGS. 1-4.

DETAILED DESCRIPTION OF THE INVENTION

Figure 1:
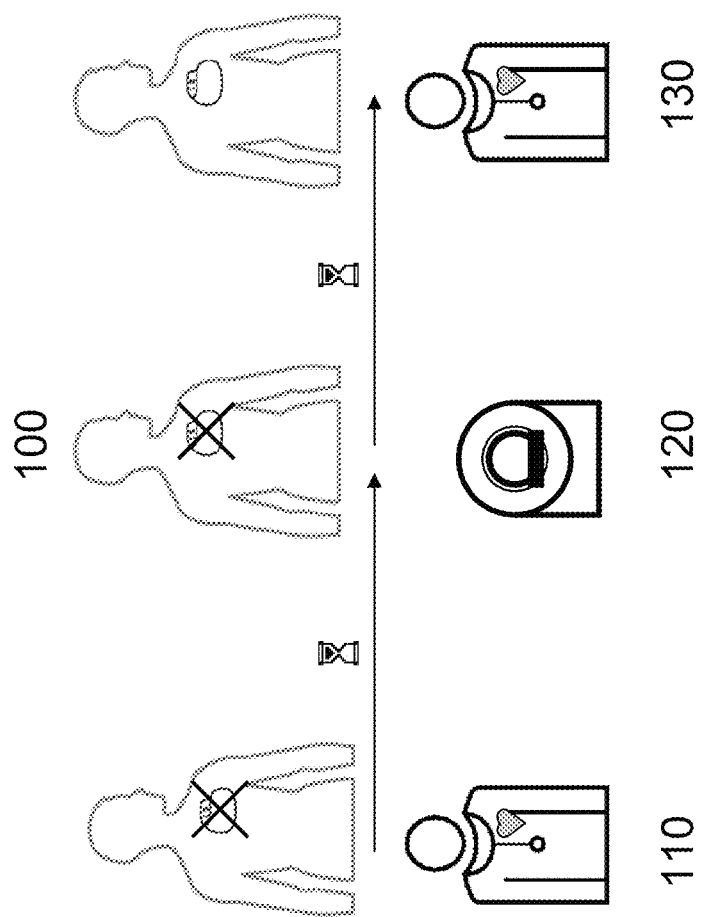
FIG. 1 schematic illustration of the progression of an MRI examination
FIG. 2 block diagram of a solution according to the invention
FIG. 3 schematic illustration of an IMD with possible positions of the vibration transducer
FIG. 4 schematic design of a Lorentz sensor.

FIG. 1 describes prior art in which the ICD patient 100 prior to the planned MRT examination is cared for by a cardiologist and the ICD 110 is switched off. At a time delay of hours to days, the MRT examination takes place by a radiologist 120. After an additional delay, the patient is again cared fore by a cardiologist 130 and the ICD is switched on again. During the entire time from 110 to 130, the patient is without the protection of the implanted defibrillator and is largely without rhythm monitoring. Currently, this remaining residual risk is accepted because of the advantage of the MRT examination.

Figure 2:
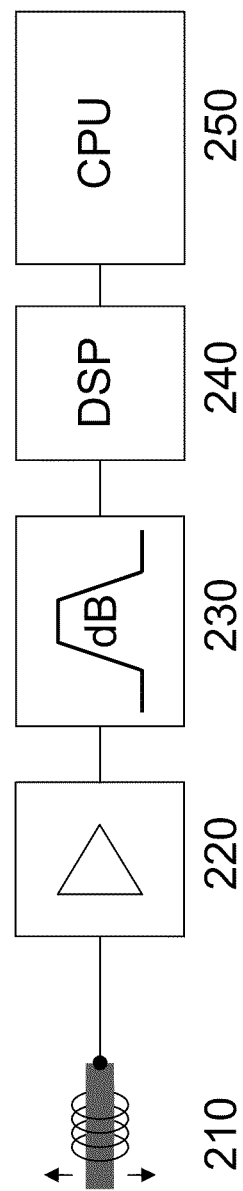

FIG. 2 shows a block diagram of the solution in accordance with the invention for detecting vibrations in the electronic implant as they are induced by an MRT device. The vibration transducer 210 is connected with an amplifier unit and a digitization unit 220. The digitized sensor signal is subsequently filtered for typical MRT frequency content 230 and subsequently analyzed in a digital signal processor 240. Thereby, for the analysis, autocorrelation and conventional procedures of speech recognition (specifically voice recognition) can be provided. If a typical MRT vibration and/or oscillation is recognized, the implant reacts with altered behavior, as it switches, controlled by a CPU/control unit 250, into a pre-programmable MRT-safe operating mode.

Figure 3:
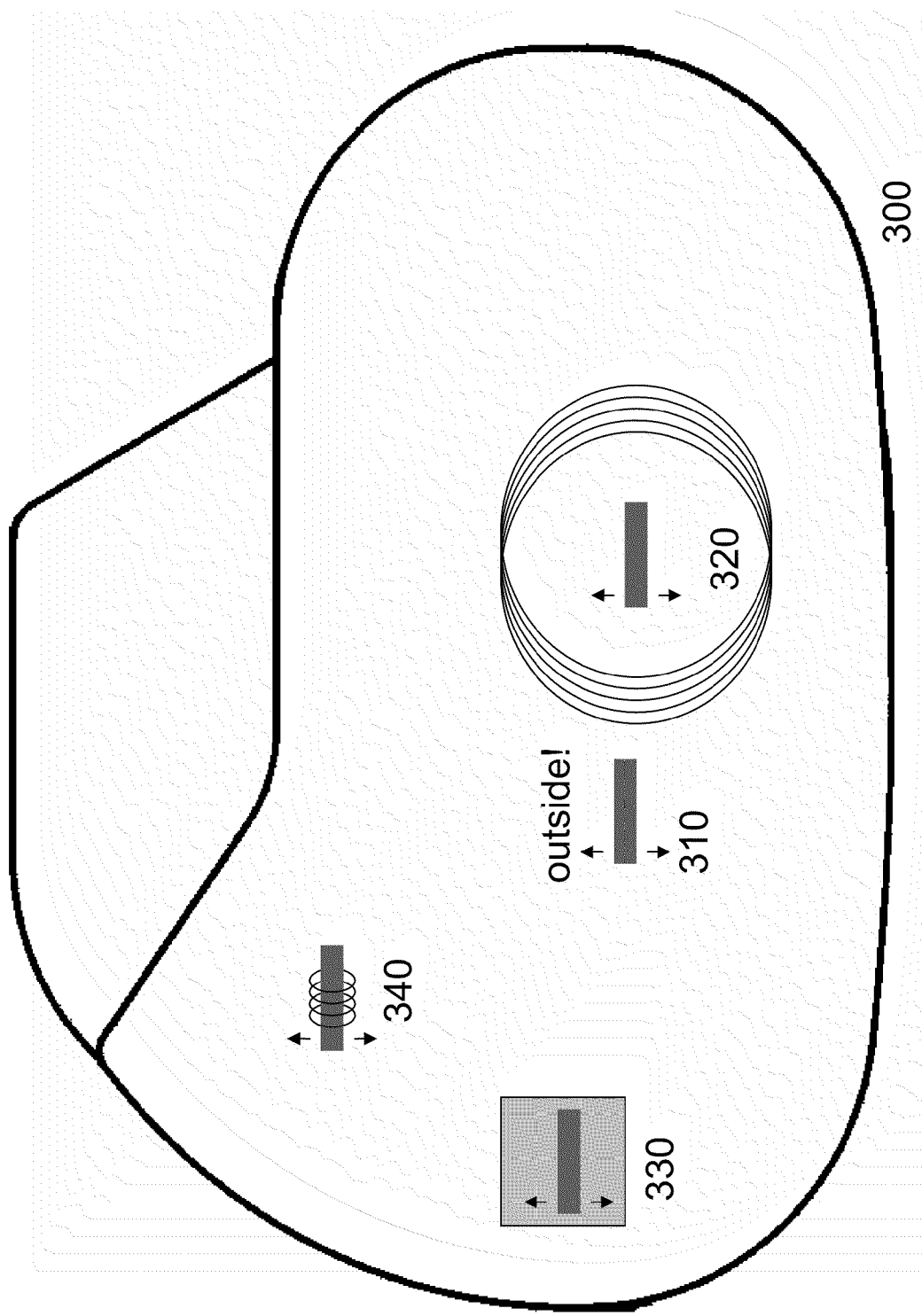

FIG. 3 shows a schematic illustration of an IMD with possible positions of the vibration transducers for the MRT vibration recognition within an electronic implants 300. The vibration transducer such as vibration transducer 210 for example can be mounted at the interior side of the housing 310, whereby here, that half of the housing that points to the exterior of the body is preferred and perhaps an instruction is to be placed onto the housing. Another option is the combination with the programmed spool 320, whereby such is then designed in such a way that the vibration preferably takes place in the spectrum of the MRT vibrations. For ICDs the vibration transducer can also be mounted at the high tension transformer 330, as it also contains a coil and thus vibration is induced in the MRT. If the vibration transducer is designed as per FIG. 4, it can be positioned freely in the interior of the implant, as it is then itself in a position to generate a vibration in the MRT.

Figure 4:
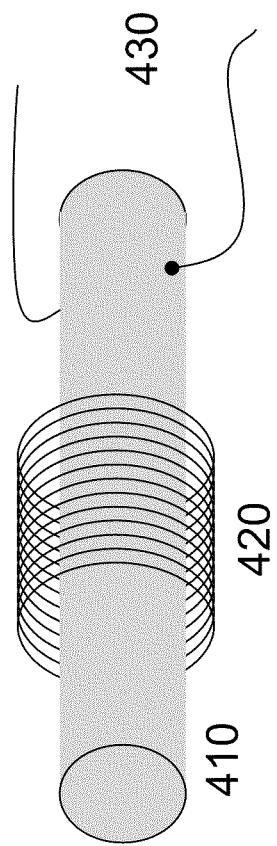

FIG. 4 shows an MRT Lorentz sensor schematically, how it can be used as vibration transducer. It consists of a piezoelectric core 410, wound with a coil 420. The sensor vibrations are captured by the input leads 430 that are connected with the core. The resonance frequency of the core and the coil are thereby dimensioned in such a way that a typical vibration is achieved in the MRT. In particular, the presence of a very strong magnetic field is taken into consideration in dimensioning. In place of the piezoelectric core material, an acceleration sensor or other adequate methods from prior art can also be used.

Embodiments of the invention make it possible to realize a reliable recognition of an MRT in electronic implants. As a result it is possible to dispense with the previously necessary reprogramming prior to and after an MRT examination. The invention makes use of the fact that the gradient fields and the static magnetic field cause the MRT vibrations that are based on the Lorentz force. These vibrations occur in the MRT device itself (typical MRT noise) as well as in the implant and can be targeted to be generated there as the result of constructive steps.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:
1. An implantable medical device comprising:
   at least one vibration transducer;
   a detector configured to detect magnetic resonance tomography activity comprising said at least one vibration transducer;
   a digital signal processor;
   wherein said at least one vibration transducer is configured to transform vibrations and oscillations created by a magnetic resonance tomography device into one or more of an electrical and optical signal;

wherein the at least one vibration transducer comprises one or more of a microphone and at least one acceleration sensor;

wherein said detector configured to detect magnetic resonance tomography activity is further configured to recognize magnetic tomography based on one or more of said electrical and said optical signal;

wherein said digital signal processor is configured to use autocorrelation such that the observed magnetic resonance tomography noises are filtered and subsequently associated with typical sequences of magnetic resonance tomography; and wherein the at least one vibration transducer, via Lorentz force, is further configured to vibrate when a magnetic field with a predeterminable minimum field strength is present simultaneously with eddy currents that are induced by alternating magnetic fields.

2. The implantable medical device according to claim 1, wherein based on recognition of magnetic resonance tomography activity, an operating mode for the implantable medical device is selected configured to permit safe operation of said implantable medical device subject to magnetic resonance tomography activity.

3. The implantable medical device according to claim 1, wherein the vibrations are one or more of results from Lorentz forces that are transmitted via electromagnetic fields from the magnetic resonance tomography device to the at least one vibration transducer; and results from Lorentz forces that are transmitted by electromagnetic fields from the magnetic resonance tomography device to the implantable medical device and from there to the at least one vibration transducer; and created in the magnetic resonance tomography device and are transmitted mechanically to the at least one vibration transducer; and, wherein with different types of transmission, one or more of the at least one vibration transducer is further configured to operate with different types of transmission, and the at least one vibration transducer comprises separate vibration transducers configured to respectively operate with the different types of transmission.

4. The implantable medical device according to claim 1, wherein the at least one vibration transducer is further configured to be adjusted to a frequency spectrum that is typical for magnetic resonance tomography noise of magnetic resonance tomography devices.

5. The implantable medical device according to claim 1, further comprises said acceleration sensor, wherein the at least one vibration transducer is configured as said acceleration sensor, wherein said acceleration sensor is configured to stimulate using rate-adaptive stimulation of one or more of a cardiac pacemakers, defibrillator/cardioverter and a cardiac resynchronization device.

6. The implantable medical device according to claim 1, wherein the at least one vibration transducer is housed in one or more of a helium-tight housing and an evacuated housing.

7. The implantable medical device according to claim 1, further comprising a high tension transformer, wherein the at least one vibration transducer is mechanically connected with said high tension transformer.

8. The implantable medical device according to claim 1, wherein the at least one vibration transducer is further configured to be connected with a programming coil of the implantable medical device, so that the programming coil vibrates by magnetic resonance tomography activity, and wherein vibrations are configured to be transmitted to the vibration transducer such that resonance behavior of the programming coil is adjusted to typical magnetic resonance tomography activities.

9. The implantable medical device according to claim 1, wherein one or more of the at least one vibration transducer comprises a piezoelectric core surrounded by a coil, whereby the coil is configured to put the piezoelectric core into vibration as a result of Lorentz forces and generates a piezoelectric signal to detect magnetic resonance tomography activity; and the at least one vibration transducer comprises an acceleration sensor as a core surrounded by a coil, wherein the core of the coil is configured to vibrate as a result of Lorentz forces.

10. The implantable medical device according to claim 1, further comprising one or more of a voice recognition object configured to recognize said magnetic resonance tomography noises or different magnetic resonance tomography noises and a neural network, wherein one or more of the voice recognition object and the neural network are configured to process the signals of the at least one vibration transducer.

11. The implantable medical device according to claim 1, wherein during magnetic resonance tomography activity, the implantable medical device is configured to change into a magnetic resonance imaging-safe condition, remain in a magnetic resonance imaging-safe or insensitive condition with respect to electromagnetic interference fields, deliver electromagnetic pulses that signal that a medical device is present in an electromagnetic field to an magnetic resonance imaging device which makes said signal visible on a monitor of the magnetic resonance imaging device, and deliver a therapy and/or detect electrical conditions of tissue only in timeframes in which no electromagnetic interference fields are recognized and/or reconstruction of measurements is performed for sections in which detection is not allowed because of recognized electromagnetic interference fields.

12. The implantable medical device according to claim 1, wherein said detector configured to detect magnetic resonance tomography activity comprises at least one of the following sensors or indicators:

GMR sensor,

MagFET sensor,

Hall sensor, electro-optical converter, battery voltage sensor configured to monitor voltage during capacitor charging, RF field detector, magnetic gradient field detector, and current detector configured to be used with currents induced by electromagnetic fields.

13. The implantable medical device according to claim 1, wherein the magnetic resonance tomography noise comprise one or more of vibrations and oscillations, caused by automated mechanical motions.

14. An implantable medical device comprising:

at least one vibration transducer;

a detector configured to detect magnetic resonance tomography activity comprising said at least one vibration transducer;

a digital signal processor;

wherein said at least one vibration transducer is configured to transform vibrations and oscillations created by a magnetic resonance tomography device into one or more of an electrical and optical signal;
wherein the at least one vibration transducer comprises one or more of a microphone and at least one acceleration sensor;
wherein said detector configured to detect magnetic resonance tomography activity is further configured to recognize magnetic tomography based on one or more of said electrical and said optical signal;
wherein said digital signal processor is configured to use autocorrelation such that the observed magnetic resonance tomography noises are filtered and subsequently associated with typical sequences of magnetic resonance tomography;
wherein during magnetic resonance tomography activity, the processor is configured to control the implantable medical device to:
change into a magnetic resonance imaging-safe condition,
remain in the magnetic resonance imaging-safe or an insensitive condition with respect to electromagnetic interference fields,
deliver electromagnetic pulses that signal that the medical device is present in an electromagnetic field to a magnetic resonance imaging device which makes said signal visible on a monitor of the magnetic resonance imaging device, and
deliver therapy and detect electrical conditions of tissue only in timeframes in which no electromagnetic interference fields are recognized and reconstruction of measurements is performed for sections in which detection is not allowed because of recognized electromagnetic interference fields; and
wherein the at least one vibration transducer, via Lorentz force, is further configured to vibrate when a magnetic field with a predeterminable minimum field strength is present simultaneously with eddy currents that are induced by alternating magnetic fields.

15. The implantable medical device according to claim 14, wherein said implantable medical device further comprising one or more of a voice recognition object configured to recognize said magnetic resonance tomography noises or different magnetic resonance tomography noises and a neural network, wherein one or more of the voice recognition object and the neural network are configured to process the signals of the at least one vibration transducer.

* * * * *